US010264790B2

(12) United States Patent
Elsherif et al.

(10) Patent No.: US 10,264,790 B2
(45) Date of Patent: Apr. 23, 2019

(54) USE OF CERTAIN HERBICIDE COMBINATIONS BASED ON IODOSULFURON IN TEFF PLANTS

(71) Applicant: BAYER CROPSCIENCE AKTIENGESELLSCHAFT, Monheim am Rhein (DE)

(72) Inventors: Mohamed Elsherif, Leverkusen (DE); Thomas Wilde, Weilrod-Hasselbach (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/466,345

(22) Filed: Mar. 22, 2017

(65) Prior Publication Data

US 2017/0273304 A1  Sep. 28, 2017

(30) Foreign Application Priority Data

Mar. 24, 2016 (EP) .................................... 16162167

(51) Int. Cl.
| | | |
|---|---|---|
| A01N 47/36 | (2006.01) | |
| A01N 25/00 | (2006.01) | |
| A01N 25/32 | (2006.01) | |
| A01N 37/06 | (2006.01) | |
| A01N 43/56 | (2006.01) | |
| A01N 39/04 | (2006.01) | |
| A01N 43/76 | (2006.01) | |
| A01N 47/38 | (2006.01) | |

(52) U.S. Cl.
CPC ............. *A01N 47/36* (2013.01); *A01N 25/00* (2013.01); *A01N 25/32* (2013.01); *A01N 37/06* (2013.01); *A01N 39/04* (2013.01); *A01N 43/56* (2013.01); *A01N 43/76* (2013.01); *A01N 47/38* (2013.01)

(58) Field of Classification Search
CPC ........ A01N 47/36; A01N 37/06; A01N 43/56; A01N 43/76; A01N 25/00; A01N 25/32; A01N 39/04; A01N 47/38
See application file for complete search history.

(56) References Cited

U.S. PATENT DOCUMENTS

| | | | |
|---|---|---|---|
| 2,606,830 | A | 8/1952 | Kamlet et al. |
| 4,130,413 | A | 12/1978 | Handte et al. |
| 4,881,966 | A | 11/1989 | Nyffeler et al. |
| 2015/0105259 | A1* | 4/2015 | Roechling ............. A01N 47/36 504/212 |

FOREIGN PATENT DOCUMENTS

| | | |
|---|---|---|
| DE | 2640730 A1 | 3/1978 |
| EP | 0002800 A1 | 7/1979 |
| EP | 0131258 A2 | 1/1985 |
| WO | 91/07874 A1 | 6/1991 |
| WO | 92/13845 A1 | 8/1992 |
| WO | 95/07897 A1 | 3/1995 |
| WO | 95/08919 A1 | 4/1995 |
| WO | 95/10507 A1 | 4/1995 |
| WO | 96/14747 A1 | 5/1996 |
| WO | 96/41537 A1 | 12/1996 |
| WO | 98/024320 A1 | 6/1998 |
| WO | 99/16744 A1 | 4/1999 |
| WO | 01/05788 A1 | 1/2001 |
| WO | 03/026426 A1 | 4/2003 |
| WO | 2013/092500 A1 | 6/2013 |
| WO | 2013/127860 A1 | 9/2013 |

OTHER PUBLICATIONS

"The e-Pesticide Manual", 14-4.0, British Crop Production Council, XP-002480840, May 20, 2008.
Davidson, Jay et al., "Response of Teff Grain Yields to Several Broadleaf Herbicides Applied at Three Different Growth Stages During 2009", Fact Sheet—10-76, University of Nevada Cooperative Extension.
Norberg, Steve et al., "Weed Efficacy and Teff Response to Selected Herbicides", Nov. 16, 2012, Washington State University.
Felix, Joel, "Evaluation of Herbicides for Possible use on Teff".
Creech, Earl et al., "Teff Hay Production Guidelines for Utah", Agriculture, Oct. 2012, Utah State University Cooperative Extension.
Mersie, Wondimagegnehu et al., "Selectrive Control of Grass Weeds in Teff with and without Use of a Safener", Tropical Pest Management, pp. 333-338, Dec. 1983, vol. 29, No. 4.
Feldt, Scott et al., "Sensitivity of Teff (*Eragrostis tef*) to Various Herbicides", North Central Weed Science Society Proceedings, 2006, vol. 61, No. 40.
Hinds-Cook, B.J. et al., "Tolerance of Teff to Herbicides", Crop and Science, Oregon State, pp. 43-44.
Norberg, O. Steven et al., "Response to Teff, Barnyardgrass, and Broadleaf Weeds to Postemergence Herbicides", Weed Technology, Apr.-Jun. 2014, pp. 371-376, vol. 28, No. 2.

* cited by examiner

*Primary Examiner* — John Pak
*Assistant Examiner* — Andriae M Holt
(74) *Attorney, Agent, or Firm* — McBee Moore Woodward & Vanik IP, LLC

(57) ABSTRACT

The present invention primarily relates to the use of specific herbicide combinations based on iodosulfuron or of a composition comprising said specific herbicide combinations for controlling harmful plants in teff (*Eragrostis tef*) plants. The present invention also relates to the use of specific herbicide combinations based on iodosulfuron or of a composition comprising said specific herbicide combinations as plant growth regulators for teff (*Eragrostis tef*) plants. Furthermore, the present invention relates to a corresponding method of controlling harmful plants in teff (*Eragrostis tef*) plants and to a corresponding method of regulating plant growth of teff (*Eragrostis tef*) plants.

16 Claims, No Drawings

USE OF CERTAIN HERBICIDE COMBINATIONS BASED ON IODOSULFURON IN TEFF PLANTS

CROSS-REFERENCE TO RELATED APPLICATION

This application claims priority to European Patent Application No. 16162167.7, filed Mar. 24, 2016. The disclosure of the priority application is incorporated in its entirety herein by reference.

BACKGROUND

Field

The present invention primarily relates to the use of specific herbicide combinations based on iodosulfuron or of a composition comprising said specific herbicide combinations for controlling harmful plants in teff (*Eragrostis tef*) plants. The present invention also relates to the use of specific herbicide combinations based on iodosulfuron or of a composition comprising said specific herbicide combinations as plant growth regulators for teff (*Eragrostis tef*) plants. Furthermore, the present invention relates to a corresponding method of controlling harmful plants in teff (*Eragrostis tef*) plants and to a corresponding method of regulating plant growth of teff (*Eragrostis tef*) plants.

Description of Related Art

Teff (*Eragrostis tef*), also called Williams lovegrass or taf, is an annual grass, a species of lovegrass native to the northern Ethiopian Highlands and Eritrean Highlands of the Horn of Africa.

Teff (*Eragrostis tef*) (hereinafter also referred to as "teff") has an attractive nutrition profile, being high in dietary fiber and iron and providing protein and calcium. Teff is adapted to environments ranging from drought stress to waterlogged soil conditions.

Teff has been widely cultivated and used in the countries of Eritrea and Ethiopia, and accounts for about a quarter of total cereal production in Ethiopia. In a study in Ethiopia, farmers indicated a preference among consumers for white teff over darker colored varieties.

Teff is gaining popularity in the western United States as an alternative forage crop, in rotation with a legume such as alfalfa, because it uses C4 photosynthesis.

Teff is an important food grain in Ethiopia and Eritrea, and less so in India and Australia. It is now raised in the U.S., in Idaho in particular, with experimental plots in Kansas. In addition to people from traditional teff-consuming countries, customers include those on gluten-restricted diets. Teff has a high concentration of different nutrients, very high calcium content, and significant levels of the minerals. Teff is high in protein and considered to have an excellent amino acid composition, including all 8 essential amino acids for humans. Teff is also valued for its fine straw, and it has been used to produce gluten free beer.

Teff is a warm-season C4 annual grass crop grown for forage and food grain that has recently increased in production in parts of the United States. Hay from teff is well suited for livestock.

Teff has long been grown for hay and grain in Ethiopia where it is a major food crop.

Weed control has been identified as the most limiting factor in attaining better teff grain yield.

Lower yields are to a large extent due to effects of weed competition or to uncontrolled or unsufficiently controlled weed growth. Hoe-weeding still is a common practice among teff farmers in many regions.

In Tropical Pest Management 1983, 29, 333-338 eleven herbicides were tested in pot experiments for the control of *Phalaris paradoxa* and *Setaria pallidefusca* in teff. Some of the herbicides used only gave partial control of these two weeds and/or did not show selectivity. Chlorsulfuron applied pre-emergence was safe on teff and controlled both weed species. Diclofop-methyl, only when applied pre-emergence with a safener, was tolerated by teff, and controlled both weeds. Other herbicides like alachlor, pendimethalin or metoxuron, with or without the safener, failed to show selectivity.

The authors of the North Central Weed Science Society Proccedings 2006, 61:40 report on the sensitivity of teff (*Eragrostis tef*) to various herbicides. It is mentioned that field studies conducted Kansas showed that post-emergence applications of 2,4-D, dicamba, bromoxynil, carfentrazone, halosulfuron, and prosulfuron resulted in less than 5% injury on teff at 8 week after treatment, whereas mesotrione, sethoxydim, and glyphosate resulted in yield reductions of 30, 50, and 99%, respectively.

In the Crop and Soil Report 14 SR 10-08, p. 43-44 of the Oregon State University the authors summarized the results observed in preliminary field studies conducted in Oregon in 2009 regarding the tolerance of teff to several herbicides. For example, mesotrione treatments resulted in 100% injury to the teff when applied preemergence. Some of the postemergence treatments caused significant injury to teff. For example, pinoxaden caused 70% injury, mesotrione caused 63% injury, nicosulfuron caused 20% injury, and mesosulfuron caused 10% injury to teff when applied postemergence. The postemergence treatments that caused little or no teff injury were inter alia metribuzin, flucarbazone, clopyralid, fluroxypyr, pyraflufen, metsulfuron, chlorsulfuron, and tribenuron. However, some of these herbicide treatments did not control the weed species spectrum present in the field. The two treatments at the site that resulted in the highest levels of weed control, teff safety and teff yields were postemergence applications of metsulfuron and chlorsulfuron.

Weed Technology 2014, (28), 371-376 reports on the tolerance of teff to post-emergence herbicides, specifically 2,4-D amine, dimethylamine salt of dicamba, carfentrazone-ethyl and a mix of florasulam, fluoroxypyr and pryoxsulam.

WO 2013/127860 A1 discloses the use of agrochemical compositions comprising at least one herbicide and at least one fungicide in cereals.

In their application, herbicidal crop protection agents (herbicides) known to date for controlling harmful plants or unwanted vegetation in teff (*Eragrostis tef*) plants have some disadvantages, be it (a) that they have no or else insufficient herbicidal activity against specific harmful plants, (b) that the spectrum of harmful plants which can be controlled with the herbicides is not broad enough, and/or (c) that the selectivity of herbicides in and the compatibility with teff (*Eragrostis tef*) plants is too low, thereby causing unwanted damage and/or unwanted reduced harvest yields of teff (*Eragrostis tef*).

Overall, the herbicidal activity (above aspects (a) and (b)) and/or the selectivity/compatibility (above aspect (c)) of the herbicides used so far in teff (*Eragrostis tef*) plants still allows improvement.

For the reasons mentioned above, there still is a need for alternative, highly active herbicides or herbicidal compositions for the selective application for controlling harmful plants or unwanted vegetation in teff (*Eragrostis tef*) plants.

SUMMARY

Surprisingly, it has now been found that certain herbicide combinations or compositions comprising said herbicide combinations exhibit the desired herbicidal activity and are able to selectively control harmful plants or unwanted vegetation in teff (*Eragrostis tef*) plants.

The present invention primarily relates to the use of a combination of herbicides (herbicide combination) or of a composition comprising a combination of herbicides (herbicide combination)
for controlling harmful plants in teff (*Eragrostis tef*) plants,
and/or
as plant growth regulators in teff (*Eragrostis tef*) plants, wherein said combination of herbicides comprises or consists of (i) iodosulfuron, its esters and/or salts thereof, (ii) one or more further herbicides and (iii) one or more safeners.

DETAILED DESCRIPTION OF A PREFERRED EMBODIMENT

The present invention further releates to the use of a composition as defined herein in the context of the present invention which additionally comprises one or more further components selected from the group consisting of formulation auxiliaries, additives customary in crop protection, and further agrochemically active compounds (i.e. agrochemically active compounds different from components (i), (ii) and (iii) as defined herein, in particular agrochemically active compounds other than the agrochemically active compounds (i), (ii-a), (ii-b), (ii-c), (ii-d), (ii-e) and (iii) defined in the context of the present invention).

However, when a combination of herbicides used in the context of the present invention consists of herbicides (i) and (ii), this means that in such a case the combination of herbicides used in the context of the present invention or the composition comprising said combination of herbicides used in the context of the present invention does not contain any further (i.e. no additional) herbicidal active ingredient, and preferably does not contain any further agrochemically active compound.

In this context, the term "further herbicidal active ingredient" and "further agrochemically active compound" refers to the herbicides and agrochemically active compounds (pesticides), respectively, listed in "The Pesticide Manual", 16th edition, The British Crop Protection Council and the Royal Soc. of Chemistry, 2012, in particular to herbicides and agrochemically active compounds (pesticides) other than active compounds (i), (ii-a), (ii-b), (ii-c), (ii-d), (ii-e) and (iii) defined in the context of the present invention.

Of particular interest in the context of the present invention is the selective control of harmful plants or unwanted vegetation in teff (*Eragrostis tef*), i.e. in areas where teff (*Eragrostis tef*) is grown or growing. The combinations of herbicides (i) and (ii) used according to the present invention show very good to excellent control of harmful plants or unwanted vegetation in teff (*Eragrostis tef*) and good to adequate selectivity in teff (*Eragrostis tef*). However, phytotoxicity of the teff (*Eragrostis tef*) plants may occur to an agronmically unacceptable extent. Therefore combinations of herbicides (i) and (ii) used according to the present invention are combined with one or more safeners as constituent (iii). The safeners, which are used in an antidotically effective amount, reduce the phytotoxic side effects of the herbicide combinations comprising herbicides (i) and (ii) used in the context of the present invention.

The herbicide combinations and the compositions comprising said herbicide combinations used in accordance with the present invention not only exhibit an excellent herbicidal activity in controlling harmful plants or unwanted vegetation in teff (*Eragrostis tef*) plants, but also show compatibility with teff (*Eragrostis tef*) plants, i.e. said herbicides do not cause significant damage or phytotoxicity (in particular at 21 days or later after treatment (DAA)) and/or unwanted reduced harvest yields.

It has been found that herbicide combinations based on constituent (i) iodosulfuron, its esters and/or salts thereof, additionally comprising one or more further herbicides as constituent (ii), and one or more safeners as constituent (iii) allow the desired herbicidal activity and selectivity in teff (*Eragrostis tef*).

The herbicide combinations used in accordance with the present invention and the compositions comprising said herbicide combinations used in accordance with the present invention allow excellent (total) weed control at an agronomically acceptable level of damage of the teff (*Eragrostis tef*) plants. Further, the type of damage observed with the herbicide combinations and the compositions comprising said herbicide combinations used in accordance with the present invention is less harmful and/or less severe, and the teff (*Eragrostis tef*) plants affected largely or fully recover from said type of damage, e.g. 21 days after treatment (DAA) with the herbicide combinations and the compositions comprising said herbicide combinations.

Further, the herbicide combinations used in accordance with the present invention and the compositions comprising said herbicide combinations used in accordance with the present invention can be used as plant growth regulators for teff (*Eragrostis tef*) plants, thereby increasing harvest yields of teff (*Eragrostis tef*) plants and/or increasing the plant growth of the teff (*Eragrostis tef*) plants (in particular the growth of the leaves of the teff (*Eragrostis tef*) plants), in each case in comparison to teff (*Eragrostis tef*) plants not treated with herbicides (untreated control).

The present invention preferably relates to the use of a combination of herbicides or of a composition comprising a combination of herbicides as defined in the context of the present invention, wherein the teff (*Eragrostis tef*) plants are red teff (*Eragrostis tef*) plants or white teff (*Eragrostis tef*) plants.

The herbicides used in the context of the present invention are known per se, and described inter alia in "The Pesticide Manual", 16th edition, The British Crop Protection Council and the Royal Soc. of Chemistry, 2012 and the literature cited therein. The herbicides used in the context of the present invention are described in more detail hereinbelow.

The herbicide combinations used in the context of the present invention and also certain compositions comprising the herbicide combinations used in the context of the present invention as such are known. The herbicide combinations used in the context of the present invention and also certain compositions comprising the herbicide combinations used in the context of the present invention are commercially available.

According to the present invention the expression "composition" includes compositions comprising a herbicide combination as defined herein, and can be used in various acceptable or agronomically typical forms and formulations, for example in a single "ready-mix" form.

The herbicides (i) and (ii) used in the herbicide combinations used in the context of the present invention and the compositions comprising the herbicide combinations used in the context of the present invention may be a combined spray mixture composed from separate formulations of the single active compounds, such as a "tank-mix", or said composition can be a combined use of the single active ingredients when applied in a sequential manner, i.e. one after the other within a reasonably short period, such as a few hours (and preferably less than 24 hours).

The herbicides (i) and (ii) used in the herbicide combinations used in the context of the present invention include all stereoisomers and their mixtures, in particular also racemic mixtures and—if enantiomers are possible—the respective biologically active enantiomer.

If, in the context of this description, the short form of the common name of an active compound is used, this includes in each case all customary derivatives, such as the esters and salts, and isomers, in particular optical isomers, in particular the commercially available form or forms. If the common name denotes an ester or salt, this in each case also comprises all other customary derivatives, such as other esters and salts, the free acids and neutral compounds, and isomers, in particular optical isomers, in particular the commercially available form or forms. If the constituents (i), (ii) and (iii) of a herbicide combination used in the context of the present invention relate to "salts", these salts are agronomically acceptable salts. The given chemical compound names denote at least one of the compounds embraced by the common name, frequently a preferred compound. In the case of sulfonamides such as sulfonylureas, salts also include the salts formed by exchanging a hydrogen atom on the sulfonamide group by a cation.

The salts of compounds used in the context of the present invention may be used in the form of the respective alkali metal salts, alkaline earth salts or ammonium salts, preferably in the form of the respective alkali metal salts, more preferably in the form of the respective sodium or potassium salts, most preferably in the form of the respective sodium salts.

Constituent (i):

Iodosulfuron, its esters and its salts are known and described for example in WO 92/13845 A1.

Preferred constituents (i) in the context of the present invention are:

Iodosulfuron (IUPAC-Name: 4-iodo-2-[(4-methoxy-6-methyl-1,3,5-triazin-2-yl)carbamoylsulfamoyl]benzoic acid, CAS Reg. No. 185119-76-0), Iodosulfuron-methyl (IUPAC-Name: methyl 4-iodo-2-[(4-methoxy-6-methyl-1,3,5-triazin-2-yl)carbamoylsulfamoyl]benzoate, CAS Reg. No. 144550-06-1) and Iodosulfuron-methyl-sodium (IUPAC-Name: sodium ({[5-iodo-2-(methoxycarbonyl)phenyl]sulfonyl}carbamoyl)(4-methoxy-6-methyl-1,3,5-triazin-2-yl)azanide, CAS Reg. No. 144550-36-71).

More preferably, constituent (i) of the combination of herbicides comprises or consists of iodosulfuron-methyl and/or iodosulfuron-methyl-sodium.

Constituent (ii):

Herbicides suitable to be used as constituent (ii) in the context of the present invention are known per se, and described inter alia in "The Pesticide Manual", 16th edition, The British Crop Protection Council and the Royal Soc. of Chemistry, 2012 and the literature cited therein. Preferred further herbicides to be used as constituent (ii) in the context of the present invention are suitable for use in monocotyledonous crops, more preferably herbicides typically used in sweet grasses.

Preferred constituents (ii) are:

Constituent (ii-a): Amidosulfuron (IUPAC-Name: 1-(4,6-dimethoxypyrimidin-2-yl)-3-mesyl(methyl)sulfamoylurea, CAS Reg. No. 120923-37-7).

Constituent (ii-b): 2,4-D (IUPAC-Name: (2,4-dichlorophenoxy)acetic acid, CAS Reg. No. 94-75-7), 2,4-D-salts (preferably 2,4-D-ammonium salts), and 2,4-D-ester (preferably 2,4-D-$C_2$-$C_8$ alkyl esters).

In particular the following 2,4-D-salts and 2,4-D-esters are advantageous: 2,4-D-ammonium [CAS Reg. No. 2307-55-3], 2,4-D-butotyl [CAS Reg. No. 1929-73-3], 2,4-D-2-butoxypropyl [CAS Reg. No. 1320-18-9], 2,4-D-3-butoxypropyl [CAS Reg. No. 1928-45-6], 2,4-D-butyl [CAS Reg. No. 94-80-4], 2,4-D-diethylammonium [CAS Reg. No. 20940-37-8], 2,4-D-dimethylammonium [CAS Reg. No. 2008-39-1], 2,4-D-diolamine [CAS Reg. No. 5742-19-8], 2,4-D-dodecylammonium [CAS Reg. No. 2212-54-6], 2,4-D-ethyl [CAS Reg. No. 533-23-3], 2,4-D-2-ethylhexyl [CAS Reg. No. 1928-43-4], 2,4-D-heptylammonium [CAS Reg. No. 37102-63-9], 2,4-D-isobutyl [CAS Reg. No. 1713-15-1], 2,4-D-isoctyl [CAS Reg. No. 25168-26-7], 2,4-D-isopropyl [CAS Reg. No. 94-11-1], 2,4-D-isopropylammonium [CAS Reg. No. 5742-17-6], 2,4-D-lithium [CAS Reg. No. 3766-27-6], 2,4-D-meptyl [CAS Reg. No. 1917-97-1], 2,4-D-methyl [CAS Reg. No. 1928-38-7], 2,4-D-octyl [CAS Reg. No. 1928-44-5], 2,4-D-pentyl [CAS Reg. No. 1917-92-6], 2,4-D-propyl [CAS Reg. No. 1928-61-6], 2,4-D-sodium [CAS Reg. No. 2702-72-9], 2,4-D-tefuryl [CAS Reg. No. 15146-99-3], 2,4-D-tetradecylammonium [CAS Reg. No. 28685-18-9], 2,4-D-triethylammonium [CAS Reg. No. 2646-78-8], 2,4-D-tris(2-hydroxypropyl)ammonium [CAS Reg. No. 18584-79-7], 2,4-D-trolamine [CAS Reg. No. 2569-01-9], 2,4-D choline salt [CAS Reg. No. 1048373-72-3] and clacyfos, a complex ester of 2,4-D (IUPAC-Name: (1RS)-1-(dimethoxyphosphinoyl)ethyl (2,4-dichlorophenoxy)acetate or dimethyl [(1RS)-1-(2,4-dichlorophenoxyacetoxy)ethyl]phosphonate, CAS Reg. No. 215655-76-8).

In particular the following 2,4-D-esters are preferred: 2,4-D-butyl (IUPAC-Name: butyl (2,4-dichlorophenoxy)acetate, CAS Reg. No. 94-80-4), 2,4-D-ethyl (IUPAC-Name: ethyl (2,4-dichlorophenoxy)acetate, CAS Reg. No. 533-23-3), 2,4-D-2-ethylhexyl (IUPAC-Name: (RS)-2-ethylhexyl (2,4-dichlorophenoxy)acetate, CAS Reg. No. 1928-43-4), 2,4-D-isobutyl (IUPAC-Name: isobutyl (2,4-dichlorophenoxy)acetate, CAS Reg. No. 1713-15-1), 2,4-D-isoctyl (IUPAC-Name: isooctyl 2-(2,4-dichlorophenoxy)acetate, CAS Reg. No. 25168-26-7), 2,4-D-isopropyl (IUPAC-Name: isopropyl (2,4-dichlorophenoxy)acetate, CAS Reg. No. 94-11-1), 2,4-D-meptyl (IUPAC-Name: (RS)-1-methylheptyl (2,4-dichlorophenoxy)acetate, CAS Reg. No. 1917-97-1), 2,4-D-octyl (IUPAC-Name: octyl (2,4-dichlorophenoxy)acetate, CAS Reg. No. 1928-44-5), 2,4-D-pentyl (IUPAC-Name: pentyl (2,4-dichlorophenoxy)acetate, CAS Reg. No. 1917-92-6), and 2,4-D-propyl (IUPAC-Name: propyl (2,4-dichlorophenoxy)acetate, CAS Reg. No. 1928-61-6).

Constituent (ii-c): Mesosulfuron (IUPAC-Name: 2-[(4,6-dimethoxypyrimidin-2-ylcarbamoyl)sulfamoyl]-α-methanesulfonamido-p-toluic acid, CAS Reg. No. 400852-66-6), and Mesosulfuron-methyl (IUPAC-Name: methyl 2-[(4,6-dimethoxypyrimidin-2-ylcarbamoyl)sulfamoyl]-α-(methanesulfonamido)-p-toluate, CAS Reg. No. 208465-21-8).

Constituent (ii-d): Fenoxaprop (IUPAC-Name: (RS)-2-[4-(6-chloro-1,3-benzoxazol-2-yloxy)phenoxy]propionic acid or (RS)-2-[4-(6-chlorobenzoxazol-2-yloxy)phenoxy]propionic acid, CAS Reg. No. 95617-09-7), Fenoxaprop-ethyl (IUPAC-Name: ethyl (RS)-2-[4-(6-chloro-1,3-benzoxazol-2-yloxy)phenoxy]propionate or ethyl (RS)-2-[4-(6-chlorobenzoxazol-2-yloxy)phenoxy]propionate, CAS Reg. No. 66441-23-4), Fenoxaprop-P (IUPAC-Name: (R)-2-[4-(6-chloro-1,3-benzoxazol-2-yloxy)phenoxy]propionic acid or (R)-2-[4-(6-chlorobenzoxazol-2-yloxy)phenoxy]propionic acid, CAS Reg. No. 113158-40-0), and Fenoxaprop-P-ethyl (IUPAC-Name: ethyl (R)-2-[4-(6-chloro-1,3-benzoxazol-2-yloxy)phenoxy]propionate or ethyl (R)-2-[4-(6-chlorobenzoxazol-2-yloxy)phenoxy]propionate, CAS Reg. No. 71283-80-2).

Constituent (ii-e): Thiencarbazone (IUPAC-Name: 4-[(4,5-dihydro-3-methoxy-4-methyl-5-oxo-1H-1,2,4-triazol-1-yl)carbonylsulfamoyl]-5-methylthiophene-3-carboxylic acid, CAS Reg. No. 936331-72-5) and Thiencarbazone-methyl (IUPAC-Name: methyl 4-[(4,5-dihydro-3-methoxy-4-methyl-5-oxo-1H-1,2,4-triazol-1-yl)carbonylsulfamoyl]-5-methylthiophene-3-carboxylate, CAS Reg. No. 317815-83-1).

Thus, preferably, constituent (ii) of the combination of herbicides comprises or consists of (ii-a) amidosulfuron, (ii-b) 2,4-D, its esters and/or salts thereof, (ii-c) mesosulfuron, its esters and/or salts thereof, (ii-d) fenoxaprop, its esters and/or salts thereof and (ii-e) thiencarbazone its esters and/or salts thereof.

Superior results in the context of the present invention, in particular with respect to the herbicidal activity against unwanted vegetation/harmful weeds in teff growing areas and the best selectivity in teff, were observed when using constituents (ii-b), (ii-d) and/or (ii-e) in the combination of herbicides used in the context of the present invention.

Therefore, more preferably, constituent (ii) of the combination of herbicides comprises or consists of (ii-b) 2,4-D, its esters and/or salts thereof (preferably 2,4-D salts or 2,4-D-alkyl esters, more preferably 2,4-D-sodium, 2,4-D-ammonium salts or 2,4-D-$C_2$-$C_8$ alkyl esters, particularly preferably 2,4-D-2-ethyhexyl ester), (ii-d) fenoxaprop, its esters and/or salts thereof (preferably fenoxaprop-ethyl or fenoxaprop-P-ethyl, more preferably fenoxaprop-P-ethyl) and/or (ii-e) thiencarbazone, its esters and/or salts thereof (preferably thiencarbazone-methyl).

Constituent (ii-a): Amidosulfuron, its esters and its salts are known and described for example in EP 0 131 258 A2.

Constituent (ii-b): 2,4-D, its esters and its salts are known and described for example in U.S. Pat. No. 2,606,830 A and the literature cited therein.

Constituent (ii-c): Mesosulfuron, its esters and its salts are known and described for example in WO 95/10507 A1.

Constituent (ii-d): Fenoxaprop, its esters and its salts are known and described for example in DE 26 40 730 A1 and EP 0 002 800 A1.

Constituent (ii-e): Thiencarbazone, its esters and its salts are known and described for example in WO 01/005788 A1.
Constituent (iii):

Safeneres suitable to be used as constituent (iii) in the context of the present invention are known per se, and described for example in WO 2013/092500 A1 on pages 87, line 25 to 100, line 25, and the literature cited therein.

Generally, all ingredients acting as safeners in monocotyledonous crops are suitable to be used as constituent (iii) in the context of the present invention.

Preferred safeneres to be used as constituent (iii) in the context of the present invention are known per se, and described inter ilia in "The Pesticide Manual", 16th edition, The British Crop Protection Council and the Royal Soc. of Chemistry, 2012 and the literature cited therein.

Constituent (iii) of the combination of herbicides is preferably selected from the group consisting of (iii-a) mefenpyr, its esters and/or salts thereof (preferably mefenpyr-diethyl), (iii-b) isoxadifen, its esters and/or salts thereof (preferably isoxadifen), (iii-c) cyprosulfamide, its esters and/or salts thereof (preferably cyprosulfamide), (iii-d) cloquintocet, its esters and/or salts thereof (preferably cloquintocet-mexyl), (iii-e) cumyluron, its esters and/or salts thereof (preferably cumyluron), (iii-f) daimuron, its esters and/or salts thereof (preferably daimuron), (iii-g) dimepiperat, its esters and/or salts thereof (preferably dimepiperat), (iii-h) fenchlorazol, its esters and/or salts thereof (preferably fenchlorazol), and (iii j) furilazol, its esters and/or salts thereof (preferably furilazol).

Particularly preferred constituents (iii) are:

Constituent (iii-a): Mefenpyr (IUPAC-Name: (RS)-1-(2,4-dichlorophenyl)-5-methyl-2-pyrazoline-3,5-dicarboxylic acid, CAS Reg. No. 135591-00-3) and Mefenpyr-diethyl (IUPAC-Name: diethyl (RS)-1-(2,4-dichlorophenyl)-5-methyl-2-pyrazoline-3,5-dicarboxylate, CAS Reg. No. 135590-91-9).

Overall, mefenpyr-diethyl showed the best efficacy as constituent (iii) in combination with constituents (i) and (ii), in particular with the constituents (i) and (ii-a), (ii-b), (ii-c), (ii-d) and/or (ii-e) as mentioned above.

Constituent (iii-b): Isoxadifen (IUPAC-Name: 4,5-dihydro-5,5-diphenyl-1,2-oxazole-3-carboxylic acid, CAS Reg. No. 209866-92-2) and Isoxadifen-ethyl (IUPAC-Name: ethyl 4,5-dihydro-5,5-diphenyl-1,2-oxazole-3-carboxylate, CAS Reg. No. 163520-33-0).

Constituent (iii-c): Cyprosulfamide (IUPAC-Name: N-[4-(cyclopropylcarbamoyl)phenylsulfonyl]-2-methoxybenzamide, CAS Reg. No. 221667-31-8).

Constituent (iii-d): Cloquintocet (IUPAC-Name: (5-chloroquinolin-8-yloxy)acetic acid, CAS Reg. No. 88349-88-6) and Cloquintocet-mexyl (IUPAC-Name: ((RS)-1-methylhexyl (5-chloroquinolin-8-yloxy)acetate, CAS Reg. No. 99607-70-2).

Constituent (iii-a): Mefenpyr, its esters and/or salts thereof are known and described for example in WO 91/07874 A1.

Constituent (iii-b): Isoxadifen, its esters and/or salts thereof are known and described for example in WO 95/07897 A1.

Constituent (iii-c): Cyprosulfamide, its esters and/or salts thereof are known and described for example in WO 99/16744 A1.

Constituent (iii-d): Cloquintocet, its esters and/or salts thereof are known and described for example in U.S. Pat. No. 4,881,966 A.

In view of their superior effects observed in the context of the present invention, combinations of herbicides are preferred comprising or consisting of
(i) iodosulfuron-methyl and/or iodosulfuron-methyl-sodium,
one or more constituents (ii) selected from the group consisting of constituent (ii-b) 2,4-D-sodium, 2,4-D-ammonium salts, and/or 2,4-D-$C_2$-$C_8$ alkyl esters (preferably 2,4-D-2-ethyhexyl ester), or constituent (ii-d) fenoxaprop-ethyl and/or fenoxaprop-P-ethyl,
and
one or more constituents (iii) selected from the group consisting of (iii-a) mefenpyr-diethyl, (iii-b) isoxadifen, (iii-c) cyprosulfamide, and (iii-d) cloquintocet-mexyl.

The best results in the context of the present invention, in particular with respect to the herbicidal activity against unwanted vegetation/harmful weeds in teff growing areas and the lowest phytotoxicity/damage on teff, i.e. the best selectivity in teff, were observed when using the following combinations of herbicides, which therefore are particularly preferred. If damage or phytotoxicity of the teff pants occurred a few days after treatment with the herbicide combinations used in accordance with the present invention, the damage was not significant, and the teff plants recovered from said damage, e.g. 21 days after treatment (DAA)), and no unwanted reduction of harvest yields was observed.

Particularly preferred in the context of the present invention is therefore a combination of herbicides comprising or consisting of
(i) iodosulfuron-methyl and/or iodosulfuron-methyl-sodium,
one or more constituents (ii) selected from the group consisting of constituent (ii-b) 2,4-D-$C_2$-$C_8$ alkyl esters (particularly preferably 2,4-D-2-ethyhexyl ester), or constituent (ii-d) fenoxaprop-ethyl or fenoxaprop-P-ethyl, particularly preferably constituent (ii) is selected from 2,4-D-2-ethyhexyl ester or fenoxaprop-P-ethyl,
and
(iii-a) mefenpyr-diethyl.

Many of the herbicide combinations used in the context of the present invention or the compositions comprising a herbicide combination as defined herein are known per se.

For example, WO 95/08919 A1 discloses combinations of iodosulfuron, its esters and/or salts thereof and certain safeners, WO 96/14747 A1 discloses combinations of mesosulfuron, its esters and/or salts thereof and certain safeners, WO 98/024320 A1 discloses combinations of mesosulfuron-methyl or salts thereof and inter alia iodosulfuron, its esters and/or salts thereof, WO 96/41537 A1 discloses combinations of iodosulfuron esters or salts thereof and other herbicides like amidosulfuron or 2,4-D, and WO 03/026426 A1 discloses combinations of thiencarbazone-methyl and iodosulfuron-methyl-sodium.

In accordance with the present invention, the herbicide combinations as defined herein or the composition comprising a herbicide combination as defined herein comprise a herbicidally effective amount of said herbicide combination and may comprise further components, for example agrochemically active compounds of a different type and/or formulation auxiliaires and/or additives customary in crop protection, or they may be employed together with these.

In accordance with the present invention, the herbicide combinations as defined herein or the composition comprising a herbicide combination as defined herein may be applied as a split application over time. Another possibility is the application of the individual herbicides (i) and (ii) or the herbicide combinations in a plurality of portions (sequential application), for example after pre-emergence applications, followed by post-emergence applications or after early post-emergence applications, followed by applications at medium or late post-emergence.

Preferred is the simultaneous or nearly simultaneous application of the herbicides (i) and (ii) as defined herein. In the latter context, a nearly simultaneous application of the herbicides (i) and (ii) as defined herein means that the herbicides of constituents (i) and (ii) are applied within 24 hours, preferably within 12 hours, more preferably within 6 hours, even more preferably within 3 hours.

In a particularly preferred embodiment, the herbicides (i) and (ii) as defined herein are used together, i.e. applied at the same time. Thus, in a particularly preferred embodiment a composition comprising the herbicides (i) and (ii) as defined herein is used. In the most preferred embodiment, a composition comprising the active ingredients (i), (ii) and (iii) as defined herein is used, i.e. most preferably all active ingredients (i), (ii) and (iii) are used at the same time.

In a preferred embodiment, the herbicides (i) and (ii) (and preferably active ingredients (i), (ii) and (iii)) used in accordance with the present invention or a composition comprising the herbicides (i) and (ii) (and preferably active ingredients (i), (ii) and (iii)) used in accordance with the present invention are only used once per season. It was found that one application per season of the herbicides (i) and (ii) (preferably active ingredients (i), (ii) and (iii)) used in accordance with the present invention or of a composition comprising the herbicides (i) and (ii) (and preferably active ingredients (i), (ii) and (iii)) used in accordance with the present invention is sufficient to achieve the effects described in the context of the present invention, in particular regarding herbicidal activity (above aspects (a) and (b)) and/or the selectivity/compatibility (above aspect (c)).

The following preferred embodiments and the effects described for the herbicides (i) and (ii) used in accordance with the present invention or a composition comprising the herbicides (i) and (ii) used in accordance with the present invention in particular apply for herbicide combinations comprising active ingredients (i), (ii) and (iii) used in accordance with the present invention, and the compositions comprising the active ingredients (i), (ii) and (iii) used in accordance with the present invention.

In a preferred embodiment, the herbicides (i) and (ii) used in accordance with the present invention or a composition comprising the herbicides (i) and (ii) used in accordance with the present invention is applied once, twice or three times per Gregorian calendar year, i.e. in one application, in two applications or in three applications per year according to the Gregorian calendar.

In a preferred embodiment, the herbicides (i) and (ii) used in accordance with the present invention or a composition comprising the herbicides (i) and (ii) used in accordance with the present invention is applied one time per Gregorian calendar year, i.e. in one application per year according to the Gregorian calendar.

In a preferred embodiment, the herbicides (i) and (ii) used in accordance with the present invention or a composition comprising the herbicides (i) and (ii) used in accordance with the present invention is applied one time in about 12 months, i.e. in one application in about 12 months.

The effects observed when using the herbicides (i) and (ii) as defined herein or a composition comprising the herbicides (i) and (ii) as defined herein allow a more potent herbicidal action, the control of hitherto uncontrolable species (activity gaps), an extended application period and/or a reduced number of required individual applications and—as a result for the user—more advantageous weed control systems both from an economical and ecological point of view.

Preferably, the active ingredients (i), (ii) and (iii) as defined herein or a composition comprising the active ingredients (i), (ii) and (iii) as defined herein are used in post-emergence applications.

Generally, in the herbicide combinations used in accordance with the present invention and in the composition comprising a herbicide combination used in accordance with the present invention the total amount by weight of constituent (ii), i.e. one or more further herbicides, is preferably used in a higher amount than constituent (i) iodosulfuron, its esters and/or salts.

Thus, in the herbicide combinations used in accordance with the present invention and in the composition comprising a herbicide combination used in accordance with the present invention the ratio by weight of the total amount of constituent (ii), i.e. one or more further herbicides, to the total amount of (i) iodosulfuron, its esters and/or salts preferably is >1, greater than 1:1, more preferably >1.5, i.e. greater than 3:2, more preferably >2, i.e. greater than 2:1, even more preferably >3, i.e. greater than 3:1.

In the herbicide combinations used in accordance with the present invention and in the composition comprising a herbicide combination used in accordance with the present invention the ratio by weight of the total amount of constituent (ii) to the total amount of (i) iodosulfuron, its esters and/or salts preferably is in the range of from 2:1 to 50:1, more preferably in the range of from 3:1 to 40:1.

Preferably, in the herbicide combinations used in accordance with the present invention and in the composition comprising a herbicide combination used in accordance with the present invention the total amount by weight of constituent (iii), i.e. one or more safeners, is used in a higher amount than constituent (i) iodosulfuron, its esters and/or salts.

In the herbicide combinations used in accordance with the present invention and in the composition comprising a herbicide combination used in accordance with the present invention the ratio by weight of the total amount of constituent (iii), i.e. the one or more safeners, to the total amount of (i) iodosulfuron, its esters and/or salts preferably is >1, greater than 1:1, more preferably >1.5, i.e. greater than 3:2, and more preferably >2, i.e. greater than 2:1.

In the herbicide combinations used in accordance with the present invention and in the composition comprising a herbicide combination used in accordance with the present invention the ratio by weight of the total amount of constituent (iii) to the total amount of (i) iodosulfuron, its esters and/or salts preferably is in the range of from 2.5:1 to 25:1, more preferably in the range of from 2.5:1 to 20:1, even more preferably in the range of from 3:1 to 18:1.

In the herbicide combinations used in accordance with the present invention and in the composition comprising a herbicide combination used in accordance with the present invention the ratio by weight of the total amount
of constituent (ii), i.e. the one or more safeners, to the total amount of (i) iodosulfuron, its esters and/or salts preferably is >1, i.e. greater than 1:1, more preferably is >2, i.e. greater than 2:1, even more preferably is >2, i.e. greater than 3:1, and
of constituent (iii), i.e. the one or more safeners, to the total amount of (i) iodosulfuron, its esters and/or salts preferably is >1, i.e. greater than 1:1, and more preferably is >2, i.e. greater than 2:1.

The preferred application rates [indicated as g a.i./ha, i.e. grams of active ingredient per hectare] of the herbicides used in the context of the present invention as defined herein are as follows:

Constituent (i):

Iodosulfuron, its esters and/or salts, preferably iodosulfuron-methyl or its sodium salt, is preferably applied at a rate in the range of 1 to 30 g a.i./ha, more preferably at a rate in the range of 1 to 20 g a.i./ha, particularly preferably at a rate in the range of 1 to 10 g a.i./ha.

Constituent (ii-a):

Amidosulfuron, its esters and/or salts, preferably amidosulfuron or its sodium salt, is preferably applied at a rate in the range of 1 to 50 g a.i./ha, more preferably at a rate in the range of 2 to 25 g a.i./ha, particularly preferably at a rate in the range of 3 to 20 g a.i./ha.

In the herbicide combinations used in accordance with the present invention and in the composition comprising a herbicide combination used in accordance with the present invention the ratio by weight of the total amount of (ii-a) amidosulfuron, its esters and/or salts, preferably amidosulfuron or its sodium salt, to the total amount of (i) iodosulfuron, its esters and/or salts, preferably iodosulfuron-methyl or its sodium salt, preferably is in the range of from 2:1 to 8:1, more preferably in the range of from 3:1 to 6:1.

Constituent (ii-b):

2,4-D, its esters and/or salts, preferably 2,4-D and the 2,4-D-esters and 2,4-D-salts defined above as being preferred, in particular 2,4-D 2-ethyhexyl ester, is preferably applied at a rate in the range of 50 to 500 g a.i./ha, more preferably at a rate in the range of 75 to 400 g a.i./ha, particularly preferably at a rate in the range of 100 to 300 g a.i./ha.

In the herbicide combinations used in accordance with the present invention and in the composition comprising a herbicide combination used in accordance with the present invention the ratio by weight of the total amount of (ii-b) 2,4-D, its esters and/or salts, preferably 2,4-D and the 2,4-D-esters and 2,4-D-salts defined above as being preferred, in particular 2,4-D 2-ethyhexyl ester, to the total amount of (i) iodosulfuron, its esters and/or salts, preferably iodosulfuron-methyl or its sodium salt, preferably is in the range of from 10:1 to 50:1, more preferably in the range of from 15:1 to 40:1.

Constituent (ii-c):

Mesosulfuron, its esters and/or salts, preferably mesosulfuron-methyl or its sodium salt, is preferably applied at a rate in the range of 2 to 30 g a.i./ha, more preferably at a rate in the range of 3 to 25 g a.i./ha, particularly preferably at a rate in the range of 5 to 20 g a.i./ha.

In the herbicide combinations used in accordance with the present invention and in the composition comprising a herbicide combination used in accordance with the present invention the ratio by weight of the total amount of (ii-c) mesosulfuron, its esters and/or salts, preferably mesosulfuron-methyl or its sodium salt, to the total amount of (i) iodosulfuron, its esters and/or salts, preferably iodosulfuron-methyl or its sodium salt, preferably is in the range of from 2:1 to 10:1, more preferably in the range of from 3:1 to 8:1.

Constituent (ii-d):

Fenoxaprop, its esters and/or salts, preferably fenoxaprop-P-ethyl, is preferably applied at a rate in the range of 10 to 125 g a.i./ha, more preferably at a rate in the range of 15 to 100 g a.i./ha, particularly preferably at a rate in the range of 25 to 75 g a.i./ha.

In the herbicide combinations used in accordance with the present invention and in the composition comprising a herbicide combination used in accordance with the present invention the ratio by weight of the total amount of (ii-d) fenoxaprop, its esters and/or salts, preferably fenoxaprop-P-ethyl, to the total amount of (i) iodosulfuron, its esters and/or salts, preferably iodosulfuron-methyl or its sodium salt, preferably is in the range of from 2:1 to 20:1, more preferably in the range of from 5:1 to 12:1.

Constituent (ii-e):

Thiencarbazone, its esters and/or salts, preferably thiencarbazone-methyl, is preferably applied at a rate in the range of 1 to 30 g a.i./ha, more preferably at a rate in the range of 1 to 20 g a.i./ha, particularly preferably at a rate in the range of 1 to 10 g a.i./ha.

In the herbicide combinations used in accordance with the present invention and in the composition comprising a herbicide combination used in accordance with the present invention the ratio by weight of the total amount of (ii-e) thiencarbazone, its esters and/or salts, preferably thiencarbazone-methyl, to the total amount of (i) iodosulfuron, its esters and/or salts, preferably iodosulfuron-methyl or its sodium salt, preferably is in the range of from 3:1 to 1:3, more preferably in the range of from 2:1 to 1:2.

Constituent (iii-a):

Mefenpyr, its esters and/or salts thereof, preferably mefenpyr-diethyl, is preferably applied at a rate in the range of 2 to 100 g a.i./ha, more preferably at a rate in the range of 5 to 75 g a.i./ha, particularly preferably at a rate in the range of 10 to 50 g a.i./ha.

In the herbicide combinations used in accordance with the present invention and in the composition comprising a herbicide combination used in accordance with the present invention the ratio by weight of the total amount of (iii-a) mefenpyr, its esters and/or salts thereof, preferably mefenpyr-diethyl, to the total amount of (i) iodosulfuron, its esters and/or salts, preferably iodosulfuron-methyl or its sodium salt, preferably is in the range of from 2:1 to 30:1, more preferably in the range of from 2.5:1 to 20:1.

Constituent (iii-c):

In the herbicide combinations used in accordance with the present invention and in the composition comprising a herbicide combination used in accordance with the present invention the ratio by weight of the total amount of (iii-c) cyprosulfamide, its esters and/or salts thereof, preferably cyprosulfamide, to the total amount of herbicides (i) and (ii) as defined herein in the herbicide combinations used in accordance with the present invention and in the composition comprising a herbicide combination, preferably is in the range of from 8:1 to 1:1, more preferably in the range of from 5:1 to 2:1.

The herbicides (i) and (ii) as defined herein more preferably applied in the more preferred rates as defined above (as defined after the term "more preferably"), and particularly preferably applied in the particularly preferred rates as defined above (as defined after the term "particularly preferably").

Furthermore, the constituents (i), (ii) and (iii) as defined herein can be used together with other agrochemically active compounds, for example from the group of the safeners, fungicides, insecticides, other herbicides and other plant growth regulators, or with formulation auxiliaries and additives customary in crop protection. Additives are, for example, fertilizers and colorants. Preference is in each case given to the ratios by weight mentioned above for each of the constituents (i), (ii) and (iii), and the application rates or the application rate ranges mentioned above for each of the constituents (i), (ii) and (iii).

Reported important weeds in teff (*Eragrostis tef*) plant fields are *Amaranthus* spp., *Avena* spp., *Chenopodium* spp., *Echinochloa* spp., *Phalaris* spp., *Portulaca* spp., *Setaria* spp. and *Solanum* spp., specifically *Amaranthus retroflexus*, *Amaranthus palmeri*, *Chenopodium album*, *Echinochloa crus-galli*, *Phalaris paradoxa*, *Portulaca oleracea*, *Setaria pallidefusca*, and *Solanum physalifolium*.

Important and relevant noxious weeds in teff (*Eragrostis tef*) plant fields in Ethiopia are *Amaranthus* spp., *Argemone* spp., *Avena* spp., *Bidens* spp., *Bromus* spp., *Chrysanthemum* spp., *Commelina* spp., *Convolvulus* spp., *Cyperus* spp., *Digitaria* spp., *Eleusine* spp., *Eragrostis* spp., *Erucastrum* spp., *Euphorbia* spp., *Foenicum* spp., *Galinsoga* spp., *Guizotia* spp., *Leucas* spp., *Lolium* spp., *Nicandra* spp., *Oxygonum* spp., *Parthenium* spp., *Phalaris* spp., *Plantago* spp., *Raphanus* spp., *Setaria* spp., *Snowdenia* spp., *Sorghum* spp. and *Xanthium* spp.

More specifically, important and relevant monocotyledonous harmful plants (grass weeds) and sedges in teff (*Eragrostis tef*) plant fields in Ethiopia are *Avena fatua*, *Bromus pectinatus*, *Cyperus esculentus*, *Cyperus rotundus*, *Digitaria abyssinica*, *Eleusine indica*, *Eragrostis aspera*, *Erucastrum arabicum*, *Lolium temulentum*, *Phalaris paradoxa*, *Setaria pumila*, *Setaria verticillata*, *Snowdenia polystachya*, and *Sorghum arundinaceum*.

More specifically, important and relevant dicotyledonous harmful plants (broadleaf weeds) in teff (*Eragrostis tef*) plant fields in Ethiopia are *Amaranthus hybridus*, *Argemone ochroleuca*, *Bidens pachyloma*, *Bidens pilosa*, *Chrysanthemum segetum*, *Commelina benghalensis*, *Convolvulus arvensis*, *Euphorbia schimperiana*, *Foenicum vulgare*, *Galinsoga parviflora*, *Guizotia scabra*, *Leucas martinicensis*, *Nicandra physalodes*, *Oxygonum sinuatum*, *Parthenium hysterophorus*, *Plantago lanceolata*, *Raphanus raphanistrum* and *Xanthium strumarium*.

The combination of herbicides as defined herein or the composition comprising a combination of herbicides as defined herein have an outstanding herbicidal activity against a broad spectrum of economically important harmful monocotyledonous and dicotyledonous harmful plants in teff (*Eragrostis tef*) plants.

In the context of the present invention "controlling" denotes a significant reduction of the growth of the harmful plant(s) in comparison to the untreated harmful plants. Preferably, the growth of the harmful plant(s) is essentially diminished (60-79%), more preferably the growth of the harmful plant(s) is largely or fully suppressed (80-100%), and in particular the growth of the harmful plant(s) is almost fully or fully suppressed (90-100%).

Preferably, the present invention relates to the use of the combination of herbicides as defined herein or the composition comprising a combination of herbicides as defined herein, wherein one, several or all harmful plants are selected from the group consisting of *Amaranthus* spp., *Argemone* spp., *Avena* spp., *Bidens* spp., *Bromus* spp., *Chenopodium* spp., *Chrysanthemum* spp., *Commelina* spp., *Convolvulus* spp., *Cyperus* spp., *Digitaria* spp., *Echinochloa* spp., *Eleusine* spp., *Eragrostis* spp., *Erucastrum* spp., *Euphorbia* spp., *Foenicum* spp., *Galinsoga* spp., *Guizotia* spp., *Leucas* spp., *Lolium* spp., *Nicandra* spp., *Oxygonum* spp., *Parthenium* spp., *Phalaris* spp., *Plantago* spp., *Portulaca* spp., *Raphanus* spp., *Setaria* spp., *Snowdenia* spp., *Solanum* spp., *Sorghum* spp. and *Xanthium* spp.

In a more specific aspect, the present invention relates to the use of the combination of herbicides as defined herein or the composition comprising a combination of herbicides as defined herein, wherein one, several or all harmful plants are selected from the group consisting of *Amaranthus* spp., *Argemone* spp., *Bidens* spp., *Bromus* spp., *Chenopodium* spp., *Cyperus* spp., *Echinochloa* spp., *Eragrostis* spp., *Erucastrum* spp., *Foenicum* spp., *Galinsoga* spp., *Lolium* spp., *Nicandra* spp., *Parthenium* spp., *Phalaris* spp., *Portulaca* spp., *Setaria* spp., *Solanum* spp., and *Sorghum* spp.

Particularly, the combination of herbicides as defined herein or the composition comprising a combination of herbicides as defined herein are used to control one, several or all harmful plants selected from the group consisting of *Amaranthus hybridus*, *Amaranthus retroflexus*, *Amaranthus palmeri*, *Argemone ochroleuca*, *Avena fatua*, *Bidens pachyloma*, *Bidens pilosa*, *Bromus pectinatus*, *Chenopodium album*, *Chrysanthemum segetum*, *Commelina benghalensis*, *Convolvulus arvensis*, *Cyperus esculentus*, *Cyperus rotundus*, *Digitaria abyssinica*, *Echinochloa crus-galli*, *Eleusine indica*, *Eragrostis aspera*, *Erucastrum arabicum*, *Euphorbia schimperiana*, *Foenicum vulgare*, *Galinsoga parviflora*, *Guizotia scabra*, *Leucas martinicensis*, *Lolium temulentum*, *Nicandra physalodes*, *Oxygonum sinuatum*, *Parthenium hysterophorus*, *Phalaris paradoxa*, *Plantago lanceolata*, *Portulaca oleracea*, *Raphanus raphanistrum*, *Setaria pallidefusca*, *Setaria pumila*, *Setaria verticillata*, *Setaria*

*viridis, Snowdenia polystachya, Solanum physalifolium, Sorghum arundinaceum* and *Xanthium strumarium*.

More specifically, the combination of herbicides as defined herein or the composition comprising a combination of herbicides as defined herein are used to control one, several or all harmful plants selected from the group consisting of *Amaranthus hybridus, Amaranthus retroflexus, Amaranthus palmeri, Argemone ochroleuca, Bidens pachyloma, Bidens pilosa, Chenopodium album, Cyperus esculentus, Cyperus rotundus, Echinochloa crus-galli, Eragrostis aspera, Erucastrum arabicum, Foenicum vulgare, Galinsoga parviflora, Nicandra physalodes, Parthenium hysterophorus, Phalaris paradoxa, Portulaca oleracea, Setaria pallidefusca, Setaria verticillata, Setaria viridis, Solanum physalifolium* and *Sorghum arundinaceum*.

In particular, the combination of herbicides as defined herein or the composition comprising a combination of herbicides as defined herein are able to control *Phalaris paradoxa*, a very important and noxious weed species in teff, in particular in some regions like Ethiopia.

If a herbicide combination used according to the present invention or if a composition comprising a herbicide combination used in the context of the present invention is applied to the soil surface before germination, then the weed seedlings are either prevented completely from emerging, or the weeds grow until they have reached the cotyledon stage but then their growth stops, and, eventually, after three to four weeks have elapsed, they die completely.

If a herbicide combination used according to the present invention or if a composition comprising a herbicide combination used in the context of the present invention is applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

The use of a herbicide combination used according to the present invention and the use of a composition comprising a herbicide combination used in the context of the present invention is characterized by a rapidly commencing and long-lasting herbicidal action.

In particular when the herbicide combinations as defined in the context of the present invention and the compositions comprising a herbicide combination as defined in the context of the present invention are employed application rates may be reduced, a broader spectrum of broad-leaved weeds and grass weeds maybe controlled, the herbicidal action may take place more rapidly, the duration of action may be longer, the harmful plants may be controlled better while using only one, or few, applications, and the application period which is possible to be extended.

The abovementioned properties and advantages are of benefit for weed control practice to keep agricultural crops free from undesired competing plants and thus to safeguard and/or increase the yields from the qualitative and quantitative point of view. These novel combinations markedly exceed the technical state of the art with a view to the properties described.

While the herbicide combinations according to the present invention have an outstanding herbicidal activity against monocotyledonous and dicotyledonous weeds, the crop plants are damaged only to a minor extent, if at all.

Moreover, some of the compositions according to the present invention have outstanding growth-regulatory properties on the crop plants. They engage in the plants' metabolism in a regulatory manner and can thus be employed for provoking directed effects on plant constituents and to facilitate harvesting such as for example by triggering desiccation and stunted growth. Moreover, they are also suitable for the general control and inhibition of undesired vegetative growth without simultaneously destroying the plants. An inhibition of vegetative growth is very important in a large number of monocotyledonous and dicotyledonous crops since yield losses as a result of lodging can thus be reduced, or prevented completely.

Owing to their herbicidal and plant-growth-regulatory properties, the compositions according to the present invention can be employed for controlling harmful plants in genetically modified crop plants or crop plants obtained by mutation/selection. These crop plants are distinguished as a rule by particular, advantageous properties, such as resistances to herbicidal compositions or resistances to plant diseases or causative agents of plant diseases such as particular insects or microorganisms such as fungi, bacteria or viruses. Other particular properties relate, for example, to the harvested material with regard to quantity, quality, storability, composition and specific constituents. Thus, for example, transgenic plants are known whose starch content is increased or whose starch quality is altered, or those where the harvested material has a different fatty acid composition.

The present invention also relates to a method of controlling undesired vegetation (e.g. harmful plants) in teff (*Eragrostis tef*) plants, which comprises applying a herbicide combination and compositions as defined in the context of the present invention or applying a composition comprising a herbicide combination as defined in the context of the present invention, for example by the pre-emergence method, by the pre-emergence and the post-emergence method, preferably by the post-emergence method to the plants, for example harmful plants, parts of these plants, plant seeds or the area where the plants grow, for example the area under cultivation.

Thus, in a further aspect, the present invention relates to a method for controlling undesired plant growth, and/or controlling harmful plants in teff (*Eragrostis tef*) plants, and/or regulating plant growth in teff (*Eragrostis tef*) plants, comprising the step of applying a combination of herbicides or a composition comprising a combination of herbicides as defined hereinabove onto the teff (*Eragrostis tef*) plants, parts of teff (*Eragrostis tef*) plants, seeds of teff (*Eragrostis tef*) plants, the area where the teff (*Eragrostis tef*) plants grow or the area where the teff (*Eragrostis tef*) plants are intended to grow.

In another aspect, the present invention relates to a method according to the present invention as defined above, wherein one, several, or all harmful plants as mentioned above are controlled.

Preferably, in a method according to the present invention as defined above, the teff (*Eragrostis tef*) plants are red teff (*Eragrostis tef*) plants or white teff (*Eragrostis tef*) plants.

In another aspect, the present invention relates to a method according to the present invention as defined abov, wherein the teff (*Eragrostis tef*) plants have been genetically modified, preferably said teff (*Eragrostis tef*) plants are transgenic plants or obtained by mutation/selection.

As already mentioned above, the herbicide combinations as defined in the context of the present invention can not only be used as mixed formulations, if appropriate together with further agrochemically active compounds, additives and/or customary formulation auxiliaries, which are then applied in the customary manner as a dilution with water, but also as so-called tank mixes by jointly diluting the separately formulated, or partially separately formulated, components with water.

The herbicide combinations as defined in the context of the present invention and the compositions comprising a herbicide combination as defined in the context of the present invention can be formulated in various ways, depending on the prevailing biological and/or chemical-physical parameters. The following are examples of general possibilities for formulations: wettable powders (WP), water-soluble concentrates, emulsifiable concentrates (EC), aqueous solutions (SL), emulsions (EW) such as oil-in-water and water-in-oil emulsions, sprayable solutions or emulsions, suspension concentrates (SC), oil dispersions (OD), oil- or water-based dispersions, suspoemulsions, dusts (DP), seed-dressing materials, granules for soil application or for broadcasting, or water-dispersible granules (WG), ULV formulations, microcapsules or waxes.

The individual formulation types are known in principle and are described for example, in: Winnacker-Küchler, "Chemische Technologie", Volume 7, C. Hauser Verlag Munich, 4$^{th}$ Edition, 1986; van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives are also known and are described, for example, in Watkins, "Handbook of Insecticide Dust Diluents and Carriers", 2nd Ed., Darland Books, Caldwell N.J.; H.v. Olphen, "Introduction to Clay Colloid Chemistry"; 2nd Ed., J. Wiley & Sons, N.Y. Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976, Winnacker-Küchler, "Chemische Technologie", Volume 7, C. Hauser Verlag Munich, 4$^{th}$ Edition 1986.

Based on these formulations, combinations with other agrochemically active substances, such as other herbicides not belonging to constituents (i) and (ii) as defined in the context of the present invention, fungicides or insecticides, and with safeners, fertilizers and/or growth regulators, may also be prepared, for example in the form of a readymix or a tank mix.

Wettable powders (sprayable powders) are products which are uniformly dispersible in water and which, besides the active compound, also comprise ionic or nonionic surfactants (wetters, dispersants), for example polyoxyethylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltauride, in addition to a diluent or inert material.

Emulsifiable concentrates are prepared by dissolving the active compound in an organic solvent, for example butanol, cyclohexanone, dimethylformamide, xylene or else higher-boiling aromatics or hydrocarbons with addition of one or more ionic or nonionic surfactants (emulsifiers). Examples of emulsifiers which may be used are: calcium salts of alkylarylsulfonic acids, such as calcium dodecylbenzene sulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxethylene sorbitol esters.

Dusts are obtained by grinding the active compound with finely divided solid materials, for example talc, natural clays such as kaolin, bentonite and pyrophyllite, or diatomaceous earth.

Suspension concentrates (SC) can be water- or oil-based. They can be prepared, for example, by wet grinding by means of commercially available bead mills and, if appropriate, addition of further surfactants as they have already been mentioned for example above in the case of the other formulation types.

Emulsions, for example oil-in-water emulsions (EW), can be prepared for example by means of stirrers, colloid mills and/or static mixers using aqueous organic solvents and, if appropriate, further surfactants as have already been mentioned for example above in the case of the other formulation types.

Granules can be prepared either by spraying the active compound onto adsorptive, granulated inert material or by applying active compound concentrates to the surface of carriers such as sand, kaolinites or granulated inert material with the aid of binders, for example polyvinyl alcohol, sodium polyacrylate or else mineral oils. Suitable active compounds may also be granulated in the manner conventionally used for the production of fertilizer granules, if desired in a mixture with fertilizers. As a rule, water-dispersible granules are prepared by customary processes such as spray drying, fluidized-bed granulation, disk granulation, mixing with high-speed mixers and extrusion without solid inert material. Regarding the production of disk granules, fluidized-bed granules, extruder granules and spray granules, see, for example, the methods in "Spray-Drying Handbook" 3rd ed. 1979, G. Goodwin Ltd., London; J. E. Browning, "Agglomeration", Chemical and Engineering 1967, page 147 et seq; "Perry's Chemical Engineer's Handbook", 5th Ed., McGraw-Hill, New York 1973, pp. 8-57.

As regards further details on the formulation of crop protection products, see, for example, G. C. Klingmam, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical formulations comprise 1 to 95% by weight, of active compounds, the following concentrations being customary, depending on the type of formulation:

The active compound concentration in wettable powders is, for example, approximately 10 to 95% by weight, the remainder to 100% by weight being composed of customary formulation constituents. In the case of emulsifiable concentrates, the active compound concentration may amount to, for example, 5 to 80% by weight. Formulations in the form of dusts comprise, in most cases, 5 to 20% by weight of active compound, sprayable solutions approximately 0.2 to 25% by weight of active compound. In the case of granules such as dispersible granules, the active compound content depends partly on whether the active compound is present in liquid or solid form and on which granulation auxiliaries and fillers are being used. As a rule, the content amounts to between 10 and 90% by weight in the case of the water-dispersible granules.

In addition, the abovementioned active compound formulations may comprise, if appropriate, the conventional adhesives, wetters, dispersants, emulsifiers, preservatives, antifreeze agents, solvents, fillers, colorants, carriers, antifoams, evaporation inhibitors, pH regulators or viscosity regulators.

The herbicidal action of the herbicide combinations according to the present invention can be improved, for example, by surfactants, preferably by wetters from the group of the fatty alcohol polyglycol ethers. The fatty alcohol polyglycol ethers preferable contain 10-18 carbon atoms in the fatty alcohol radical and 2-20 ethylene oxide units in the polyglycol ether moiety. The fatty alcohol polyglycol ethers can be nonionic or ionic, for example in the form of fatty alcohol polyglycol ethers sulfates, which can be used, for example, as alkali metal salts (e.g. sodium salts or potassium salts) or ammonium salts, but also as alkaline earth metal salts such as magnesium salts, such as sodium $C_{12}/C_{14}$-fatty alcohol diglycol ether sulfate (Genapol® LRO, Clariant); see, for example, EP-A-0476555, EP-A-0048436, EP-A-0336151 or U.S. Pat. No. 4,400,196 and also Proc. EWRS Symp. "Factors Affecting Herbicidal Activity and Selectivity", 227-232 (1988). Nonionic fatty alcohol polyglycol ethers are, for example, $(C_{10}-C_{18})$—, preferably $(C_{10}-C_{14})$-fatty alkohol polyglycol ethers containing 2-20, preferably 3-15, ethylene oxide units (e.g. isotridecyl alcohol polyglycol ether), for example from the Genapol® series, such as Genapol® X-030, Genapol® X-060, Genapol® X-080 or Genapol® X-150 (all from Clariant GmbH).

The present invention furthermore embraces the combination of herbicides (i) and (ii) as defined above with the wetting agents mentioned above from the group of the fatty alcohol polyglycolethers which preferably contain 10-18 carbon atoms in the fatty alcohol radical and 2-20 ethylene oxide units in the polyglycol ether moiety and which can be present in nonionic or ionic form (for example as fatty alcohol polyglycol ether sulfates). Preference is given to $C_{12}/C_{14}$-fatty alcohol diglycol ether sulfate sodium (Genapol® LRO, Clariant); and isotridecyl alcohol polyglycol ether with 3-15 ethylene oxide units, for example from the Genapol® X series, such as Genapol® X-030, Genapol® X-060, Genapol® X-080 or Genapol® X-150 (all from Clariant GmbH). It is furthermore known that fatty alcohol polyglycol ethers such as nonionic or ionic fatty alcohol polyglycol ethers (for example fatty alcohol polyglycol ether sulfates) are also suitable for use as penetrants and activity enhancers for a number of other herbicides, inter alia also for herbicides from the group of the imidazolinones (see, for example, EP-A-0502014).

Moreover, it is known that fatty alcohol polyglycol ethers such as nonionic or ionic fatty alcohol polyglycol ethers (for example fatty alcohol polyglycol ether sulfates) are also suitable as penetrants and synergists for a number of other herbicides, inter alia also herbicides from the group of the imidazolinones; (see, for example, EP-A-0502014).

The herbicidal effect of the herbicide combinations according to the present invention can also be increased using vegetable oils. The term vegetable oils is to be understood as meaning oils from oil-plant species, such as soya oil, rapeseed oil, corn oil, sunflower oil, cottonseed oil, linseed oil, coconut oil, palm oil, safflower oil or castor oil, in particular rapeseed oil, and their transesterification products, for example alkyl esters, such as rapeseed oil methyl ester or rapeseed oil ethyl ester.

The vegetable oils are preferably esters of $C_{10}$-$C_{22}$—, preferably $C_{12}$-$C_{20}$-fatty acids. The $C_{10}$-$C_{22}$-fatty acid esters are, for example, esters of unsaturated or saturated $C_{10}$-$C_{22}$-fatty acids, in particular those with an even number of carbon atoms, for example erucic acid, lauric acid, palmitic acid and, in particular, $C_{18}$-fatty acids such as stearic acid, oleic acid, linoleic acid or linolenic acid.

Preferred $C_1$-$C_{20}$-alkyl-$C_{10}$-$C_{22}$-fatty acid esters are the methyl, ethyl, propyl, butyl, 2-ethylhexyl and dodecyl esters. Preferred glycol- and glycerol-$C_{10}$-$C_{22}$-fatty acid esters are the uniform or mixed glycol esters and glycerol esters of $C_{10}$-$C_{22}$-fatty acids, in particular those fatty acids which have an even number of carbon atoms, for example erucic acid, lauric acid, palmitic acid and, in particular, $C_{18}$-fatty acids such as stearic acid, oleic acid, linolic acid or linolenic acid.

The vegetable oils can be present in the herbicidal compositions according to the present invention for example in the form of commercially available oil-containing formulation additives, in particular those based on rapeseed oil such as Hasten® (Victorian Chemical Company, Australia, hereinbelow termed Hasten, main constituent: rapeseed oil ethyl ester), Actirob®B (Novance, France, hereinbelow termed ActirobB, main constituent: rapeseed oil methyl ester), Rako-Binol® (Bayer AG, Germany, termed Rako-Binol hereinbelow, main constituent: rapeseed oil), Renol® (Stefes, Germany, termed Renol hereinbelow, vegetable oil constituent: rapeseed oil methyl ester), or Stefes Mero® (Stefes, Germany, hereinbelow termed Mero, main constituent: rapeseed oil methyl ester).

In a further embodiment, the present invention embraces the combination of a herbicide combination as defined in the context of the present invention with the vegetable oils mentioned above. Thus, in a further embodiment, the present invention embraces the use of compositions comprising a herbicide combination as defined in the context of the present invention comprising the vegetable oils mentioned above, such as rapeseed oil, preferably in the form of commercially available oil-containing formulation additives, in particular those based on rapeseed oil such as Hasten® (Victorian Chemical Company, Australia, hereinbelow termed Hasten, main constituent: rapeseed oil ethyl ester), Actirob®B (Novance, France, hereinbelow termed ActirobB, main constituent: rapeseed oil methyl ester), Rako-Binol® (Bayer AG, Germany, termed Rako-Binol hereinbelow, main constituent: rapeseed oil), Renol® (Stefes, Germany, termed Renol hereinbelow, vegetable oil constituent: rapeseed oil methyl ester), or Stefes Mero® (Stefes, Germany, hereinbelow termed Mero, main constituent: rapeseed oil methyl ester).

For use, the formulations, which are present in commercially available form, are optionally diluted in the customary manner, for example using water in the case of wettable powders, emulsifiable concentrates, dispersions and water-dispersible granules. Preparations in the form of dusts, soil granules, granules for broadcasting and sprayable solutions are usually not diluted further with other inert substances prior to use.

The active compounds can be applied to the plants, parts of the plants, seeds of the plants or the area under cultivation (soil of a field), preferably to the green plants and parts of the plants and, if appropriate, additionally to the soil of the field.

A composition comprising a herbicide combination used in the context of the present invention has the advantage of being easier to apply, and the quantities of the components are advantageously already presented in the correct ratio to each other. Moreover, the adjuvants in the formulation can be matched optimally to each other.

Examples

1. Products Used

The following products—all compositions comprising a herbicide combination according to the present invention—were tested:

Product P1 contained 25 g/l iodosulfuron-methyl-sodium, 100 g/l amidosulfuron and 250 g/l mefenpyr-diethyl (OD-formulation)

Product P2 contained 2 g/l iodosulfuron-methyl-sodium, 10 g/l mesosulfuron-methyl and 30 g/l mefenpyr-diethyl (OD-formulation)

Product P3 contained 8 g/l iodosulfuron-methyl-sodium, 64 g/l fenoxaprop-P-ethyl and 24 g/l mefenpyr-diethyl (EC-formulation)

Product P4 contained 10 g/l iodosulfuron-methyl-sodium, 250 g/l 2,4-D-2-ethylhexyl and 30 g/l mefenpyr-diethyl (OD-formulation)

2. Biological Trials 2.1 Trials in the Greenhouse

Greenhouse trials with the respective products P1, P2, P3 or P4 were conducted on teff plants in direct comparison to *Setaria viridis* (SETVI), a plant—like teff—also beloning to the Pocaceae family.

The Tables 1 and 2 reflect the observations after certain periods of time, indicated in days (referred to as DAA=days after application) after start of a single treatment with/application of the respective product P1, P2, P3 or P4 mentioned above, each in the amounts indicated below.

The ratings for the damage and herbicidal activity each were performed on a scale of 0-100%, wherein 100% means that all (weed) plants had died in the respective pot, whereas 0% damage or herbicidal activity means that no damage or herbicidal activity was observed in comparison to the respective untreated control pot.

Table 1 reflects the damage/phytotoxicity observed on red teff plants for the different products applied once after 10 and 21 days, respectively, after treatment (DAA).

Table 2 reflects the respective observed herbicidal activity ratings after start of a single treatment of the harmful plant species *Setaria viridis* (SETVI) for the different products applied once in post-emergence.

TABLE 1

Damage ratings of red teff plants in pots treated once with the respective product 10 and 21 days after treatment (DAA), respectively

| Product | Amount of Product applied | Damage of red teff in % 10 DAA | Damage of red teff in % 21 DAA |
|---|---|---|---|
| P1 | 0.15 L/ha | 15 | 0 |
| P1 | 0.075 L/ha | 0 | 0 |
| P2 | 0.625 L/ha | 40 | 0 |
| P3 | 0.50 L/ha | 43 | 20* |
| P4 | 1.00 L/ha | 0 | 0 |
| P4 | 2.00 L/ha | 2 | 2 |

*In a subsequent field trial, no relevant damage/phytotoxicity was observed.

TABLE 2

Ratings of herbicial activity against SETVI in pots treated post-emergence once with the respective product 10 and 21 days after treatment (DAA), respectively

| Product | Amount of Product applied | Control of SETVI in % 10 DAA | Control of SETVI in % 21 DAA |
|---|---|---|---|
| P1 | 0.15 L/ha | 88 | 72.5 |
| P2 | 1.25 L/ha | 85 | 90 |
| P2 | 0.625 L/ha | 85 | 85 |
| P3 | 1.00 L/ha | 75 | 75 |
| P4 | 1.00 L/ha |  | 45 |
| P4 | 2.00 L/ha |  | 73 |

2.2 Trials in the Field

In field trials conducted at several different locations, the herbicidal activity of the respective products P1, P2, P3 or P4 was investigated against different weed species.

The field trials were conducted in neighbouring plots under identical conditions (apart from the treatment with the different products P1 to P4 mentioned above). Depending on the location, different harmful plant species (weed species) were present and the activity of products P1 to P4, respectively, against the different weed species was assessed.

The ratings of the herbicidal activity were performed on a scale of 0-100%, wherein 100% activity means that all weed plants had died in the respective plot, 50% herbicidal activity means that the weed coverage in the respective plot has been reduced by 50% in comparison to the untreated control plot, and 0% activity means that no herbicidal activity was observed in the respective plot in comparison to the untreated control plot.

Table 3 reflects the respective observed herbicidal activity ratings in field trials after treatment of the harmful plant species for the different products applied once in post-emergence.

The following codes are used for the different harmful plant species (weed species):

| Code | Weed species Scientific Name |
|---|---|
| AMARE | *Amaranthus retroflexus* |
| LOLMU | *Lolium multiflorum* |
| LOLPE | *Lolium perenne* |
| PHAPA | *Phalaris paradoxa* |
| SETPF | *Setaria pallidefusca* |

TABLE 3

Ratings of herbicial activity against different weeds in field trials treated once post-emergence with the respective product

| Product | P1 | P2 | P3 | P4 |
|---|---|---|---|---|
| Amount of Product applied | 0.15 L/ha | 0.50 L/ha | 1.00 L/ha | 1.00 L/ha |
| Weed | % Control | % Control | % Control | % Control |
| AMARE | 100 | 100 | n.a. | n.a. |
| LOLMU | 51 | 88 | 87 | 68 |
| LOLPE | 93 | 81 | 42 | 100 |
| PHAPA | n.a. | 94 | 97 | n.a. |
| SETPF | n.a. | n.a. | n.a. | 80 | n.a.: weed species not present in/no data available from the respective field trials

The invention claimed is:

1. A method for controlling harmful plants in teff (*Eragrostis tef*) plants, and/or regulating plant growth in teff (*Eragrostis tef*) plants,
    comprising applying a combination of (i) iodosulfuron, its esters and/or salts thereof, (ii) a second herbicide, and (iii) mefenpyr or its diethyl ester
    onto the teff (*Eragrostis tef*) plants, seeds of the-teff (*Eragrostis tef*) plants, and/or the area where the teff (*Eragrostis tef*) plants grow,
    wherein the second herbicide (ii) is selected from the group consisting of (ii-a) amidosulfuron, wherein the weight ratio of the total amount of constituent (ii-a) to the total amount of constituent (i) is 3:1 to 6:1, (ii-b) 2,4-D, its esters and/or salts thereof, wherein the weight ratio of the total amount of constituent (ii-b) to the total amount of constituent (i) is 15:1 to 40:1, (ii-c) mesosulfuron, its esters and/or salts thereof, wherein the weight ratio of the total amount of constituent (ii-c) to the total amount of constituent (i) is 3:1 to 8:1, and (ii-d) fenoxaprop, its esters and/or salts thereof, wherein the weight ratio of the total amount of constituent (ii-d) to the total amount of constituent (i) is 5:1 to 12:1; and wherein the total amount of constituent (iii) to the total amount of constituent (i) is 2.5:1 to 20:1.

2. A method according to claim 1, wherein constituent (i) comprises iodosulfuron-methyl and/or iodosulfuron-methyl-sodium.

3. A method according to claim 1, wherein constituent (ii) is (ii-b) 2,4-D, its esters and/or salts thereof, and/or (ii-d) fenoxaprop, its esters and/or salts thereof.

4. A method according to claim 1, wherein said combination comprises
   (i) iodosulfuron-methyl and/or iodosulfuron-methyl-sodium,
   one or more constituents (ii) selected from the group consisting of constituent (ii-b) 2,4-D-sodium, 2,4-D-ammonium salts, 2,4-D-$C_2$-$C_8$ alkyl esters, constituent (ii-d) fenoxaprop-ethyl and fenoxaprop-P-ethyl
   and
   (iii) mefenpyr-diethyl.

5. A method according to claim 4, wherein the combination does not include any other herbicides or safeners besides those recited.

6. A method according to claim 1, wherein said combination comprises
   (i) iodosulfuron-methyl and/or iodosulfuron-methyl-sodium,
   one or more constituents (ii) selected from the group consisting of constituent (ii-b) 2,4-D-$C_2$-$C_8$ alkyl esters, constituent (ii-d) fenoxaprop-ethyl, and fenoxaprop-P-ethyl,
   and
   (iii) mefenpyr-diethyl.

7. A method according to claim 6, wherein the combination does not include any other herbicides or safeners besides those recited.

8. A method according to claim 1, wherein the combination additionally comprises one or more further components selected from the group consisting of formulation auxiliaries, additives customary in crop protection, and further agrochemically active compounds.

9. A method according to claim 1, wherein one, several or all harmful plants are controlled and are selected from the group consisting of *Amaranthus* spp., *Argemone* spp., *Avena* spp., *Bidens* spp., *Bromus* spp., *Chenopodium* spp., *Chrysanthemum* spp., *Commelina* spp., *Convolvulus* spp., *Cyperus* spp., *Digitaria* spp., *Echinochloa* spp., *Eleusine* spp., *Eragrostis* spp., *Erucastrum* spp., *Euphorbia* spp., *Foenicum* spp., *Galinsoga* spp., *Guizotia* spp., *Leucas* spp., *Lolium* spp., *Nicandra* spp., *Oxygonum* spp., *Parthenium* spp., *Phalaris* spp., *Plantago* spp., *Portulaca* spp., *Raphanus* spp., *Setaria* spp., *Snowdenia* spp., *Solanum* spp., *Sorghum* spp. and *Xanthium* spp.

10. A method according to claim 1, wherein one, several or all harmful plants are controlled and are selected from the group consisting of *Amaranthus hybridus, Amaranthus retroflexus, Amaranthus palmeri, Argemone ochroleuca, Avena fatua, Bidens pachyloma, Bidens pilosa, Bromus pectinatus, Chenopodium album, Chrysanthemum segetum, Commelina benghalensis, Convolvulus arvensis, Cyperus esculentus, Cyperus rotundus, Digitaria abyssinica, Echinochloa crusgalli, Eleusine indica, Eragrostis aspera, Erucastrum arabicum, Euphorbia schimperiana, Foenicum vulgare, Galinsoga parviflora, Guizotia scabra, Leucas martinicensis, Lolium temulentum, Nicandra physalodes, Oxygonum sinuatum, Parthenium hysterophorus, Phalaris paradoxa, Plantago lanceolata, Portulaca oleracea, Raphanus raphanistrum, Setaria pallidefusca, Setaria pumila, Setaria verticillata, Setaria viridis, Snowdenia polystachya, Solanum physalifolium, Sorghum arundinaceum* and *Xanthium strumarium*.

11. The method according to claim 1, wherein one, several, or all harmful plants are controlled.

12. The method according to claim 1, wherein the teff (*Eragrostis tef*) plants are red teff (*Eragrostis tef*) plants or white teff (*Eragrostis tef*) plants.

13. The method according to claim 1, wherein said combination is applied post-emergence to the harmful plants.

14. A method according to claim 1, wherein harmful plants are controlled by treating the teff plants.

15. A method according to claim 1, wherein the plant growth of the teff plants is regulated.

16. A method according to claim 1, wherein the herbicides in the combination consist of) (i) iodosulfuron, its esters and/or salts thereof and one or more of (ii-a) amidosulfuron, (ii-b) 2,4-D, its esters and/or salts thereof, (ii-c) mesosulfuron, its esters and/or salts thereof, and/or (ii-d) fenoxaprop, its esters and/or salts thereof.

* * * * *